United States Patent [19]

Nakamura et al.

[11] 4,145,139
[45] Mar. 20, 1979

[54] ZIG ZAG SCANNING DENSITOMETER WITH BASE LINE AND IMPURITY CORRECTION

[75] Inventors: Kengi Nakamura; Hiroshi Yamamoto, both of Kyoto, Japan

[73] Assignee: Shimadzu Seisakusho Ltd., Kyoto, Japan

[21] Appl. No.: 828,545

[22] Filed: Aug. 29, 1977

[30] Foreign Application Priority Data

Aug. 31, 1976 [JP] Japan .......................... 51/117454[U]

[51] Int. Cl.² .......................................... G01N 21/22
[52] U.S. Cl. ...................................... 356/73; 356/444
[58] Field of Search .................................. 356/73, 203

[56] References Cited

U.S. PATENT DOCUMENTS 3,994,587  11/1976  Yamamoto et al. .................. 356/73
4,013,364  3/1977  Nakano et al. ........................ 356/73

Primary Examiner—John K. Corbin
Assistant Examiner—B. Y. Arnold
Attorney, Agent, or Firm—Fidelman, Wolffe & Waldron

[57] ABSTRACT

Densitometer for quantitative determination of a sample spot on a thin-layer chromatography (TLC) plate or the like having besides the spot an area of impurities developed thereon, wherein the surface of the plate is scanned in a zigzag way by a light beam having a minute cross section. In one stroke of the zigzag scanning of the area containing impurities immediately before the spot the measured signal is integrated and stored by a first integrator and in each and every one of the succeeding strokes of the scanning of the spot the measured signal is integrated by a second integrator. The stored integrated value of the first integrator is subtracted from the integrated value of the second integrator in each and every one of the scanning strokes across the spot and the result of the subtraction is integrated for quantitative determination of the spot without errors caused by the impurities contained in the sample.

10 Claims, 6 Drawing Figures

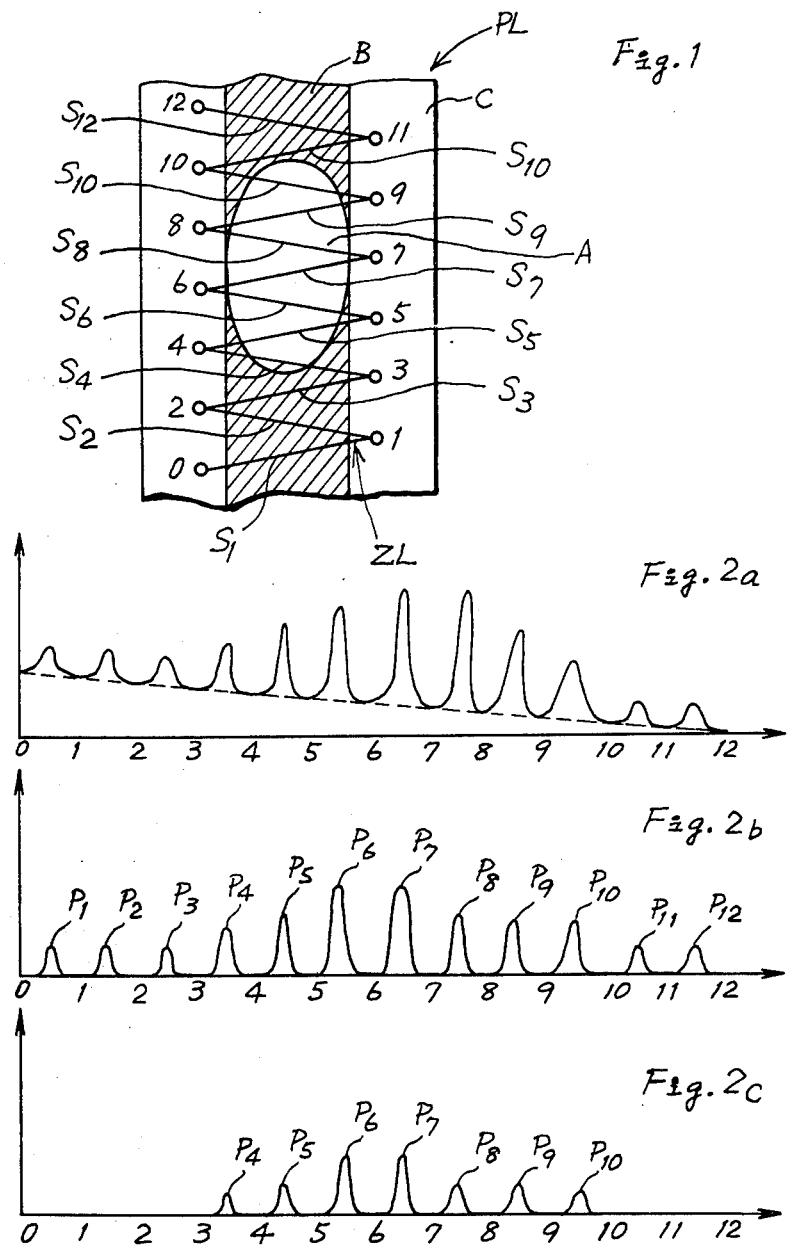

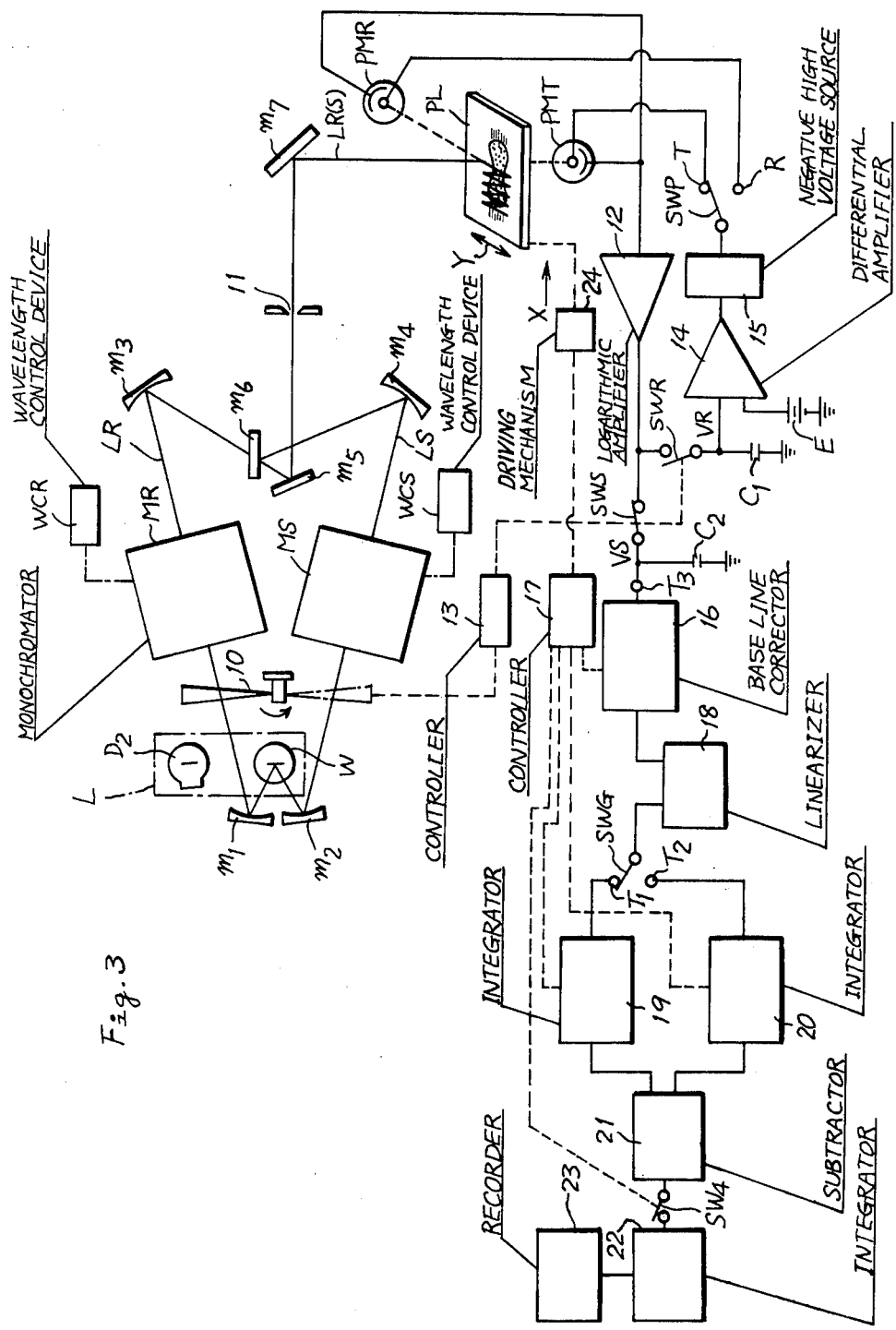

ZIG ZAG SCANNING DENSITOMETER WITH BASE LINE AND IMPURITY CORRECTION

This invention relates to a densitometer of the zigzag scanning type which uses a scanning light beam having a minute cross section for quantitative determination of spots of substances developed on a support used in thin-layer chromatography (TLC), paper chromatography, etc. with a high degree of accuracy and precision and good reproducibility.

For analysis of the component in a spot developed on a TLC plate by a densitometer of the zigzag scanning type, the spot is scanned in a zigzag way by a light beam having a minute cross section and the light transmitted through or reflected or scattered by the spot is detected to produce a corresponding electrical signal, so that the profile of the density distribution of the component substance contained in the spot is obtained or the quantity of the substance is determined by integrating the signal.

The TLC plate comprises, for example, a glass plate coated with silica gel on which each of the components of a sample is developed and separated as a spot. The nonuniformity of the TLC plate itself and/or the development of the solvent used for development of the sample affect the measured signal so that the base line thereof fluctuates in the direction of development of the solvent. When the signal is integrated, errors caused by the base line fluctuation are introduced into the result of the integration so that accurate quantitative determination of the sample components cannot be expected.

In order to eliminate the adverse influence of the base line fluctuation on the result of measurement, there has been proposed in U.S. Pat. No. 4,013,364 a method of base line correction by which at a predetermined point outside the spot in each stroke of the zigzag scanning the measured signal is periodically sampled and stored so as to be subtracted from the measured signal during the succeeding scanning stroke for correction of the base line of the measured signal.

This method is effective in case the composition of the sample developed on the supporting medium is relatively simple but if it is complex, such as powdered earthworm, a stripe of impurities which originally are the components of the sample but inseparable is produced extending in the direction of development of the sample components, so that the signal obtained outside the spot to be measured will have a peak where there should occur no such peak and the peak of the signal caused by the spot to be measured will contain a component caused by the impurities. Therefore, even when the errors caused by the nonuniformity of the thin-layer of the TLC plate and/or the nonuniformity of development of the solvent thereon have been eliminated from the measured signal, there still remain in the signal those errors which are caused by the impurities, so that accurate quantitative determination of the component of the spot cannot be effected.

Accordingly, the primary object of the invention is to provide a desnitometer of the zigzag scanning type which is capable of direct quantitative determination of the substance contained in a TLC spot with a high degree of accuracy and precision by eliminating from the measured signal errors caused by base line fluctuation and also those caused by impurities contained in the sample. To accomplish the object, the densitometer of the invention comprises: means for projecting monochromatic light onto a sample spot to be measured developed on a supporting medium; scanning means for effecting a relative zigzag movement between said monochromatic light and said supporting medium so that said monochromatic light scans along a zigzag locus a predetermined area of said supporting medium including said sample spot; photoelectric means for detecting the intensity of the light from said scanned area to produce a first electrical signal corresponding to said intensity of said light; first integrating means for integrating said first electrical signal produced during one scanning stroke when said light scans a predetermined area of said supporting medium before said sample spot, said area including impurities; second integrating means for integrating said first electrical signal produced during each scanning stroke when said light scans said sample spot; and means for subtracting the result of said integration by said first integrating means from the result of said integration by said second integrating means to produce a second electrical signal corresponding to the result of said subtraction. Preferably the densitometer of the invention further includes a base line corrector comprising means for periodically sampling the value of said first electrical signal produced when said light scans outside said sample spot and said area including impurities and correcting means for subtracting said sampled value from said first electrical signal produced in each scanning stroke before the next sampling.

The invention will be described in detail with reference to the accompanying drawings, wherein;

FIG. 1 is a schematic top plan view of a TLC plate;

FIG. 2a is the waveform of the measured signal obtained by the zigzag scanning of FIG. 1 without any correction having been made;

FIG. 2b is the waveform of the same signal as in FIG. 2a with the base line thereof having been corrected;

FIG. 2c is the waveform of the same signal as in FIG. 2a with not only the base line but also the errors caused by the impurities contained in the sample having been corrected;

FIG. 3 is a schematic deiagram of a densitometer constructed in accordance with the invention.

Figure 4:
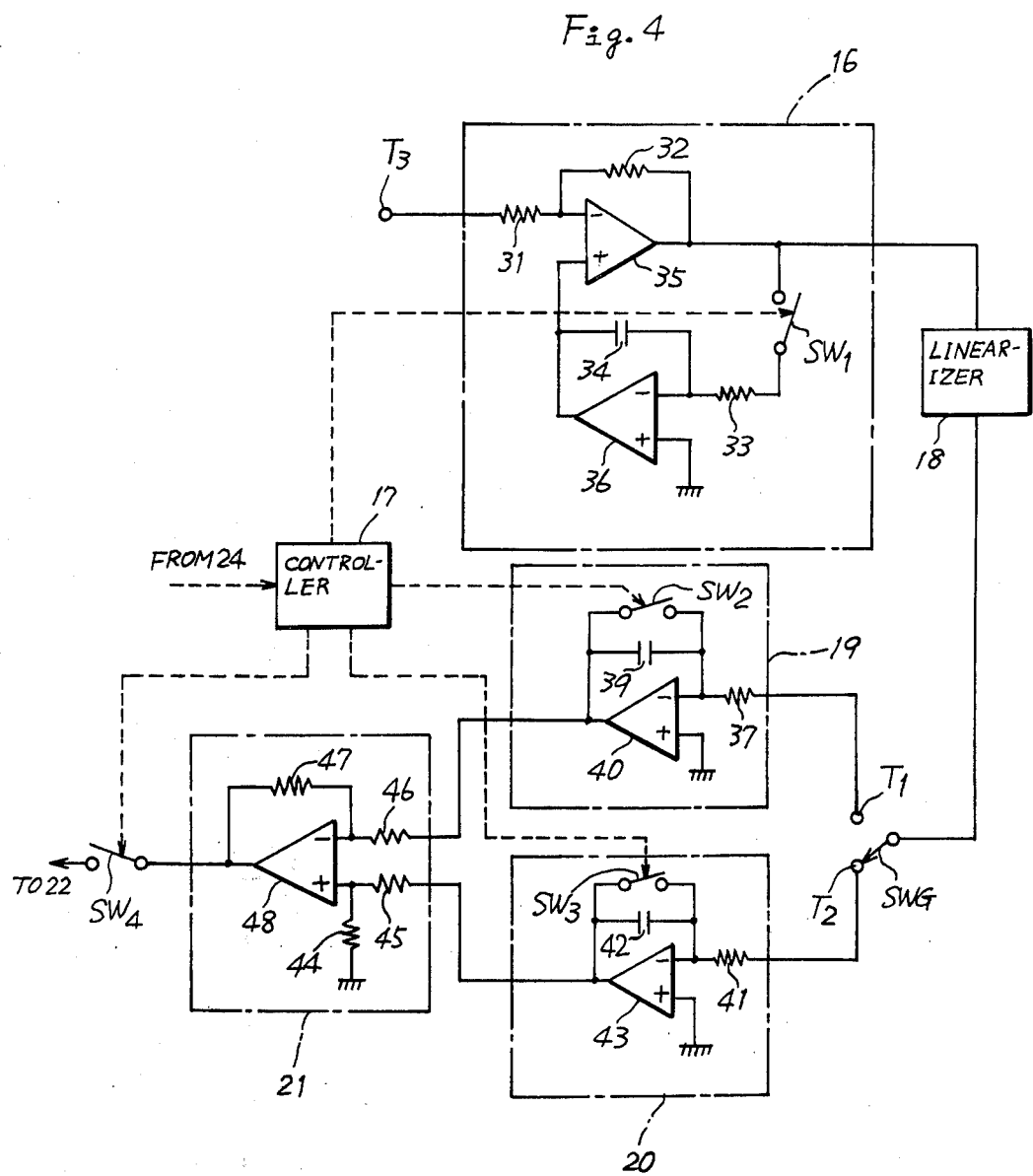
FIG. 4 is a circuit diagram of a principal portion of FIG. 3.

Referring now in detail to the drawings, first to FIG. 1, there is shown a TLC plate PL such as a glass plate coated with a thin layer of, for example, silica gel. On the plate there is developed a spot A containing a separated component of a sample to be measured, with an area B containing impurities dispersed almost uniformly in the direction of development of the sample and an area C containing the solvent only used for development of the sample.

A light beam having a minute cross section is caused to scan the plate along a zigzag locus ZL. The light from the plate is measured to produce a corresponding electrical signal. If the measured signal is plotted without any correction, an absorbance curve is obtained as shown in FIG. 2a with the base line changing. If the base line change is corrected, the curve will be plotted as shown in FIG. 2b, which still includes errors caused by impurities. If the errors caused by the impurities as well as the base line change are eliminated, the curve will be plotted as shown in FIG. 2c. The densitometer of the invention is intended for quantitative determination of the spot based on such an absorbance signal as shown in FIG. 2c.

FIG. 3 shows a schematic diagram of a densitometer of the dual-wavelength zigzag scanning type constructed in accordance with the invention. A light source L comprises a tungsten lamp W and a deuterium lamp D2, with a suitable switching device for effecting selective use of either one of the two lamps for the visible or ultraviolet region. The light from the source L is reflected by two collimating mirrors m1 and m2 so as to be introduced into two monochromators MR and MS, with a rotating chopper 10 alternately intercepting the light entering the monochromators.

The monochromators produce two monochromatic light beams LR and LS of different wavelengths selected by wavelength control devices WCR and WCS, respectively. The two light beams are reflected by concave mirrors m3 and m4, respectively, and caused by a half-mirror m6 to alternately impinge on a plane mirror m5 to be passed through a slit 11 and directed by a plane mirror m7 onto a TLC plate PL perpendicularly thereto.

A driving mechanism 24 such as disclosed in U.S. Pat. Nos. 3,994,587 and 4,013,364 moves the plate PL at a predetermined constant speed relative to the beam linearly in the direction X longitudinal of the plate, that is, in the direction of development of the sample components. Simultaneously with this movement the plate PL is linearly reciprocally moved at a constant speed horizontally in the direction Y perpendicular to the above-mentioned direction X of movement. It will be easily understood that as the plate PL is moved in the above manner, it is scanned by the light beam in a zigzag way.

The relative zigzag movement between the beam and the plate may be effected otherwise, for example, by reciprocating the light beam along the Y-axis while moving the plate linearly along the X-axis.

A photodetector PMT such as a photomultiplier tube detects the light transmitted through the plate PL, while another photodetector PMR detects the light reflected by the plate PL. The output terminals of the photomultiplier tubes are connected to the input of a logarithmic amplifier 12, the output of which is connected to a signal separating device such as a pair of switches SWS and SWR for taking out the outputs from the amplifier 12 caused by the sample and reference beams LS and LR, respectively. To this end, the switches SWS and SWR are ganged with the chopper 10 through a suitable controller 13 so that when the chopper passes the light from the source L to enter the monochromator MR while blocking it from the other monochromator MS, the switch SWR is closed and the switch SWS is opened, while when the chopper allows the light from the source to enter the monochromator MS while blocking it from the monochromator MR, the switch SWS is closed and the switch SWR is opened.

A capacitor C1 stores the reference beam signal VR when the switch SWR is closed, and a capacitor C2 stores the sample beam signal VS when the switch SWS is closed. The signal VR is also applied to a differential amplifier 14, to which a voltage source E provides a reference voltage. The output of the amplifier 14 controls a negative high voltage source 15 in such a manner that the difference input (VR - E) to the amplifier 14 becomes zero.

A switch SWP is provided to selectively actuate one of the photomultiplier tubes PMT and PMR. When the movable arm of the switch SWP is brought into contact with a terminal T, the photomultiplier tube PMT is energized to detect the light transmitted through the TLC plate PL, while when the arm is switched over to a terminal R, the photomultiplier tube PMR is energized to detect the light reflected by the plate.

When the switch SWS is closed, the absorbance signal or reflection absorbance signal from the logarithmic amplifier 12 is applied to a base line corrector 16, which corrects the base line fluctuation of the measured signal caused by the variation or nonuniformity of the supporting medium and/or development of the solvent used for developing the sample spot. The base line corrector 16 is controlled by a controller 17 which operates in response to the driving mechanism 24 of the TLC plate 24.

The base-line-corrected output from the circuit 16 is applied to a linearizer 18. In densitometrical measurement of a spot developed on a TLC plate or like supporting medium, the scanning light is scattered by the supporting medium so that the measured absorbance value is not proportional to the concentration or quantity of the substance contained in the spot. The linearizer is so designed as to compensate the absorbance or reflection absorbance signal thereby to render the signal proportional to the true absorbance or reflection absorbance of the separated sample component in the TLC spot under measurement. For detailed explanation of the principle of operation and construction of the linearizer 18 reference should be made to U.S. Pat. No. 3,994,587.

The output of the linearizer is applied through a switch SWG to a first integrator 19 or alternatively to a second integrator 20. With the movable arm of the switch SWG in contact with a terminal T1, the first integrator 19 integrates the output of the linearizer produced during one scanning stroke when the light beam scans the area B before the spot A in the direction of development thereof on the TLC plate PL, and stores the integrated value. When the arm is switched over to the other terminal T2, the second integrator 20 integrates the output of the linearizer in each and every scanning stroke while the light beam scans the spot A.

A subtractor 21 subtracts the integrated value stored in the first integrator 19 from the integrated value of the second integrator 20 in each stroke of the scanning of the spot A.

The output of the subtractor 21 is applied through a switch SW4 to an integrator 22, the output of which is read on a recorder 23.

The controller 17 operates in response to the position of the scanning beam relative to the plate PL in its zigzag scanning to control the base line corrector 16 the integrators 19 and 20 and the switch SW4 in the manner to be described later.

As previously described, when a TLC plate with a sample spot developed thereon as shown in FIG. 1 is scanned by a light beam having a minute cross section compared with the area of the spot, a profile curve of the absorbance as shown in FIG. 2a is obtained, wherein the base line gradually inclines downwardly due to the nonuniformity of development of the solvent used for developement of the sample spot, so that the curve does not express the true absorbance of the sample component under measurement.

In order to correct the base line change, the base line corrector 16 operates in the following manner. At the end designated by a small circle of each stroke of the zigzag movement of the scanning beam, the measured absorbance signal is sampled so as to serve as a new base line for the measured signal during the succeeding scanning stroke. To put it in detail, at a point "0" outside the spot A and the area B the measured signal is sampled and stored so that the stored sampled value is used as a base line for the measured signal during the succeeding scanning stroke S1 until the next sampling is conducted at point "1" at the opposite end of the stroke. In other words, the sampled value at point "0" is subtracted from the measured value of the signal during the scanning stroke S1, and at point "1" the signal is again sampled and stored so as to serve as a new base line for the measured signal during the next scanning stroke S2. In this manner, as the zigzag scanning proceeds, the sampling point is transferred from point "0" to "1", from "1" to "2" and so on, so that the base-line corrected profile curve of the absorbance shown in FIG. 2b is obtained.

In the profile curve of FIG. 2b, however, the peaks P1, P2, P3, P11 and P12 are caused by the impurities in the area B, and the peaks caused by the sample spot A are also influenced by the impurities. In accordance with the invention, the influence of the impurities can be eliminated in the following manner.

With the movable arm of the switch SWG in contact with the terminal T1, the output of the linearizer 18 corresponding to one of the peaks obtained by scanning the area B containing the impurities before the spot A is applied to the integrator 19 so as to be integrated and stored therein. To put it otherwise, the integrator 19 integrates the output from the linearizer 18 produced during one stroke of scanning the area B before the spot A and stores the integrated value.

When the scanning stroke S3 immediately before the spot A has been finished, the arm of the switch SWG is switched over to the other terminal T2, so that the second integrator 20 integrates the output of the linearizer produced in each of the succeeding strokes S4 through S10. At the end of each of the scanning strokes S4 to S10, the integrator 20 applies the integrated value for the stroke just finished to the subtractor 21, to which the integrator 19 also applies the stored integrated value obtained in the scanning stroke S3 as previously mentioned. The subtractor subtracts the latter integrated value from the former integrated value to produce an output corresponding to the result of the subtraction. This output corresponds to the integrated value of each of the peaks P4 through P10 in FIG. 2c.

When the integrator 20 has completed the integration of the measured signal produced during each of the scanning strokes S4 through S10, the switch SW4 is closed for a predetermined short period of time, so that the output from the subtractor 21 is applied to the integrator 22 to be integrated thereby. Upon lapse of the period of time the switch SW4 is opened, whereupon the integrator 20 is reset.

Suppose that the scanning stroke S4 has now been finished at point 4. The integrator 20 is reset, whereupon the next scanning stroke S5 starts at point 4, and the same operation as mentioned above is repeated so that the next peak P5 of the absorbance signal is integrated. When the last scanning stroke S10 across the spot A has been finished, integration of the absorbance signal as expressed by the profile curve shown in FIG. 2c has been completed with the adverse influences by the solvent, the impurities, etc. having been completely eliminated from the integrated value, which gives a correct quantiative determination of the sample component in the spot. The result of the integration is read on the recorder 23.

The controller 17 operates in response to the operation of the driving mechanism 24 for effecting a relative zigzag movement between the scanning light beam and the TLC plate to control the operations of the base line corrector 16, the integrators 19 and 20 and the switch SW4 in the above-mentioned sequential manner.

The mechanism for effecting the relative zigzag movement is disclosed by way of example in U.S. Pat. Nos. 3,994,587 and 4,013,364 and can advantageously be used in the densitometer of this invention.

FIG. 4 shows an example of the detailed circuit arrangements of the base line corrector 16, the first and second integrators 19 and 20 and the subtractor 21. The base line corrector 16 comprises resistors 31, 32 and 33, a switch SW1, a capacitor 34 and operational amplifiers 35 and 36. The base line corrector 16 may be replaced by the one disclosed in U.S. Pat. No. 4,013,364.

The first integrator 19 comprises a resistor 37, a switch SW2, a capacitor 39 and an operational amplifier 40; the second integrator 20 comprises a resistor 41, a switch SW3, a capacitor 42 and an operational amplifier 43; and the subtractor 21 comprises resistors 44, 45, 46 and 47 and an operational amplifier 48.

At each of the sampling points "0" through "12" laterally outside the area B and the spot A the controller 17 causes the switch SW1 to be temporarily closed so that the absorbance signal at the terminal T3 caused by the solvent at the sampling point is charged into the capacitor 34 to be stored therein, whereupon the switch SW1 is opened, so that the charged sampled signal is subtracted from the absorbance signal measured in the course of the succeeding stroke of the zigzag scanning.

With the switch SWG closed to the side of the terminal T1, the controller 17 causes the switch SW2 of the first integrator 19 to be opened at the starting point of one stroke, say, S3 of the zigzag scanning across the area B before the spot A, so that the base-line-corrected signal from the corrector 16 is applied through the linearizer 18 and the switch SWG to the first integrator 19 to be charged in the capacitor 39.

When the integration of the signal by the first integrator 19 for that one scanning stroke has been finished, the arm of the switch SWG is switched over to the other terminal T2 and the controller causes the switch SW3 of the second integrator 20 to be opened at the start of each and every one of the succeeding zigzag scanning strokes S4 to S12 and closed at the end thereof, so that the absorbance signal measured during each and every one of the scanning strokes is integrated.

The subtractor 21 subtracts the integrated output of the first integrator 19 from that of the second integrator 20 in each of the scanning strokes S4 to S12 and produces an output corresponding to the result of the subtraction.

The output of the subtractor 21 is applied through the switch SW4 to the integrator 22 to be integrated thereby. The integrated value shows the accurate quantity of the sample component under measurement contained in the spot, from which the errors due to the solvent, the impurities, etc. have been completely eliminated.

In the above explanation, the first integrator 19 operates to integrate the absorbance signal produced during the scanning stroke S3 immediately before the spot A. The scanning stroke during which the first integrator 19 integrates the signal may also be S2 or S1. By monitoring the variation of the peak value of the absorbance signal produced during each stroke of the zigzag scanning over a TLC plate it is possible to locate the position of the sample spot to be measured and then cause the first integrator to automatically perform integration of the signal in the scanning stroke immediately before the spot.

In the above described embodiment, the sampling point for base line correction is at the end of the scanning stroke, but the point may be midway in the stroke provided that it is outside the spot A and the area B. The sampling for base line correction need not always be conducted in each and every stroke of the scanning but it may be conducted once every several scanning strokes provided that the pitch of the zigzag scanning is relatively small.

What we claim is:

1. A densitometer comprising: means for projecting monochromatic light onto a sample spot developed on a supporting medium; scanning means for effecting a relative zigzag movement between said monochromatic light and said supporting medium so that said monochromatic light scans along a zigzag locus a predetermined area of said supporting medium including said sample spot; photoelectric means for detecting the intensity of the light from said scanned area to produce a first electrical signal corresponding to said intensity of said light; first integrating means for integrating said first electrical signal produced during one scanning stroke when said light scans a predetermined area of said supporting medium before said sample spot, said area including impurities other than the component of said sample spot; second integrating means for integrating said first electrical signal produced during each scanning stroke while said light scans said sample spot; and means for subtracting the result of said integration by said first integrating means from the result of said integration by said second integrating means to produce a second electrical signal corresponding to the result of said subtraction.

2. The densitometer of claim 1, further including means for periodically sampling the value of said first electrical signal produced when said light scans outside said sample spot and said area including impurities; and correcting means for subtracting said sampled value from said first electrical signal produced in each stroke of said scanning before the next sampling.

3. The densitometer of claim 2, further including a third integrating means for integrating said second electrical signal.

4. The densitometer of claim 3, further including means for reading the output of said third integrating means.

5. The densitometer of claim 1, further including a third integrating means for integrating said second electrical signal.

6. The densitometer of claim 5, further including means for reading the output of said third integrating means.

7. The densitometer of claim 1, wherein said first integrating means integrates said first electrical signal produced during the scanning stroke immediately before said sample spot.

8. The densitometer of claim 1, wherein said supporting medium is a thin-layer chromatographic plate.

9. The denistometer of claim 1, wherein said supporting medium is a sheet of filter paper in paper chromatography.

10. The densitometer of claim 1, wherein said supporting medium is an electrophoretic supporting medium.